United States Patent
Matsumura

(10) Patent No.: US 6,380,450 B1
(45) Date of Patent: Apr. 30, 2002

(54) PROCESS FOR PRODUCING INDENE

(75) Inventor: Yasuo Matsumura, Yokohama (JP)

(73) Assignee: Nippon Petrochemicals Company, Limited, Tokyo (JP)

( * ) Notice: Subject to any disclaimer, the term of this patent is extended or adjusted under 35 U.S.C. 154(b) by 0 days.

(21) Appl. No.: 09/529,510

(22) PCT Filed: Aug. 18, 1999

(86) PCT No.: PCT/JP99/04431

§ 371 Date: Apr. 15, 2000

§ 102(e) Date: Apr. 15, 2000

(87) PCT Pub. No.: WO00/10949

PCT Pub. Date: Mar. 2, 2000

(30) Foreign Application Priority Data

Aug. 18, 1998 (JP) .......................................... 10-247831
Aug. 18, 1998 (JP) .......................................... 10-247832

(51) Int. Cl.[7] .......................... C07C 5/32; C07C 5/367; C07C 5/333
(52) U.S. Cl. ...................... 585/444; 585/319; 585/320; 585/360; 585/379; 585/441; 585/444; 585/445; 585/315; 585/321
(58) Field of Search ................................. 585/319, 320, 585/360, 379, 441, 444, 445; 502/315, 321

(56) References Cited

U.S. PATENT DOCUMENTS

| 4,143,082 A | 3/1979 | Bartek et al. ................. 585/320 |
| 4,291,181 A | 9/1981 | Kiikka et al. ................ 585/320 |
| 4,292,455 A | 9/1981 | Bartek et al. ................. 585/400 |

FOREIGN PATENT DOCUMENTS

JP  54-39060  3/1979

*Primary Examiner*—Thuan D. Dang
(74) *Attorney, Agent, or Firm*—Hollander Law Firm, P.L.C.

(57) ABSTRACT

Tetrahydroindene is dehydrogenated in a vapor phase in the presence of a metallic catalyst, e.g., a nickel-molybdenum catalyst, to produce indene, which is industrially useful in high yield while inhibiting the catalyst from suffering a decrease in activity. In particular, a higher yield can be attained by a method in which tetrahydroindene is dehydrogenated to first convert it into indane, which is further dehydrogenated to obtain indene.

18 Claims, No Drawings

PROCESS FOR PRODUCING INDENE

TECHNICAL FIELD

The present invention relates to a novel process for producing indene, which is industrially useful as a raw material for producing transparent and highly heat-resistant resin or as a raw material for ligands of single site catalyst for use in the polymerization to prepare polyolefin.

BACKGROUND ART

Various methods for producing indene have hitherto been proposed.

A method of recovering indene from coal tar fraction is known. The coal tar fraction, however, contains various impurities such as benzonitrile and benzofuran. By means of recovery by distillation, it is difficult to obtain highly pure indene by separating benzonitrile, which has a boiling point close to that of indene. It is also proposed to separate indene by causing benzonitrile to react in coal tar fraction. This method, however, is economically unfavorable because of the increase in production steps.

Tetrahydroindene (hereinafter referred to as "THI") is produced as a by-product in a large quantity, for example, in various kinds of Diels-Alder reaction in chemical industry. Even though its effective uses have been desired, it is rarely used in practice.

Among few uses of THI, there is a proposed method to obtain indene by dehydrogenating THI in the presence of cobalt-molybdenum oxide catalyst as disclosed in U.S. Pat. No. 4,291,181. This method is considered to be suitable for the effective uses of THI, because obtained indene is a useful material in various utilities, in addition, inexpensive metallic catalyst is used and the reaction in itself is dehydrogenation that can be carried out without difficulty.

Although this method has an advantage that high purity indene is obtained and the degree of conversion of THI is high, it has a defect that the yield is low with the cobalt-molybdenum oxide catalyst and further, the deterioration in catalytic activity is conspicuous.

As a result of intensive investigation done by inventors of the present invention concerning the causes of the above disadvantage, it was found out that, under dehydrogenation conditions of THI in which indene is formed in high proportion, THI easily decomposes into cyclopentadiene (hereinafter referred to as "CPD") and 1,3-butadiene (hereinafter simply referred to as "butadiene") due to reverse Diels-Alder reaction of the raw material THI itself, and as a result, the yield of indene is lowered, and further that catalytic activity is lowered due to the coking caused by formed indene.

In view of these circumstances, it is an object of the present invention to provide a process to produce indene in high yield at low cost using THI as a raw material and to suppress the deterioration of catalytic activity.

DISCLOSURE OF INVENTION

A first aspect of the present invention relates to a process for producing indene and/or indane in high yield with less degree of deterioration in catalytic activity, which comprises the step of dehydrogenating tetrahydroindene in vapor phase in the presence of a metallic dehydrogenation catalyst.

A second aspect of the present invention relates to a process for producing indene as described in the first aspect of the invention, in which the dehydrogenation is carried out at temperatures of 100° C. or higher using a solid catalyst containing oxides of nickel and molybdenum as the metallic dehydrogenation catalyst.

A third aspect of the present invention relates to a process for producing indene as described in the second aspect of the invention, in which the dehydrogenation is carried out at temperatures in the range of 420° C. to 530° C.

A fourth aspect of the present invention relates to a process for producing indene as described in the second aspect of the invention, in which the dehydrogenation is carried out in the range of a pressure below atmospheric to 10 kg/cm$^2$.

A fifth aspect of the present invention relates to a process for producing indene as described in the first aspect of the invention, which comprises the following first step and second step.

(First Step) A process for producing a reaction product containing mainly indane while suppressing the formation of indene by dehydrogenating tetrahydroindene in vapor phase in the presence of metallic dehydrogenation catalyst, and (Second Step) a process for producing indene by dehydrogenating the reaction product obtained in the first step in vapor phase in the presence of metallic dehydrogenation catalyst.

A sixth aspect of the present invention relates to a process for producing indene as described in the fifth aspect of the invention, in which the content of indane of reaction product obtained in the first step is 70% by weight or more.

A seventh aspect of the present invention relates to a process for producing indene as described in the fifth aspect of the invention, in which the content of indene of reaction product obtained in the first step is 10% by weight or less.

An eighth aspect of the present invention relates to a process for producing indene as described in the fifth aspect of the invention, in which the metallic catalyst used in the first step is metallic oxide catalyst containing molybdenum oxide.

A ninth aspect of the present invention relates to a process for producing indene as described in the eighth aspect of the invention, in which the metallic dehydrogenation catalyst used in the first step is metallic oxide catalyst containing oxides of nickel and molybdenum or metallic oxide catalyst containing oxides of cobalt and molybdenum.

A tenth aspect of the present invention relates to a process for producing indene as described in the fifth aspect of the invention, in which the metallic dehydrogenation catalyst used in the second step is metallic oxide catalyst containing oxide of at least one metal selected from the group consisting of nickel, molybdenum, cobalt and chromium.

An eleventh aspect of the present invention relates to a process for producing indene as described in the tenth aspect of the invention, in which the metallic dehydrogenation catalyst used in the second step is catalyst containing oxides of nickel and molybdenum or oxides of cobalt and molybdenum.

A twelfth aspect of the present invention relates to a process for producing indene as described in the fifth aspect of the invention, in which the metallic dehydrogenation catalyst used in the second step is catalyst containing ruthenium.

The present invention will be described in more detail.

THI used in the present invention may be anyone that is obtained through any method. For example, it can be synthesized by Diels-Alder reaction of butadiene with dicyclopentadiene (hereinafter referred to as "DCPD") or CPD.

This Diels-Alder reaction can proceed by heating 1 mol of butadiene and ½ mol of DCPD or 1 mol of CPD. Although the reaction can be promoted by using an acid or other catalyst, heating is usually sufficient. The reaction temperature is in the range of 70 to 270° C. In the recovered fractions, impurities having boiling points higher than that of THI such as DCPD, methyl tetrahydroindene, or norbornene-type olefin of ethylidene norbornene, or Diels-Alder adduct of DCPD and CPD, are sometimes contained as well as THI.

As described above, by-products formed in a variety of industrial Diels-Alder reaction can also be used as raw material of THI for the present invention besides the one obtained by a process to produce THI itself.

For example, EBH (5-ethylidene-2-norbornene) is produced in a large quantity as a third monomer for producing EPDM (ethylene-propylene-diene ternary copolymer), while its intermediate product of vinyl norbornene (5-vinyl-2-norbornene) is synthesized under conditions similar to those of the above by the Diels-Alder reaction of butadiene with DCPD or CPD. THI is contained in the residue of its crude reaction product after the recovery of vinyl norbornene by distillation.

Also in this case, the above residue sometimes contains impurities having boiling points higher than that of THI such as DCPD, methyl tetrahydroindene, norbornene-type olefin of ethylidene norbornene, and adducts of Diels-Alder reaction of DCPD and CPD, besides THI.

Besides the production of vinyl norbornene, there are some cases in which by-products containing THI and other components can be obtained. In accordance with the method of the present invention, such THI materials containing other components can be used. However, purity of THI is preferably 50% or more, and more preferably more than 90% that is obtained by fractionation.

While, vinyl norbornene is easily isomerized into THI by heating to about 100° C. in the presence of metallic dehydrogenation catalyst. Therefore, vinyl norbornene can also be used as a raw material for the present invention as long as it is isomerized into THI in the process of the present invention. Moreover, the mixture of THI and vinyl norbornene can also be used as a raw material for the present invention.

In the first place, the foregoing methods of the second to fourth aspect of the present invention will be described in more detail.

Solid catalyst used in dehydrogenation of the present invention comprises oxides of nickel and molybdenum. For example, solid catalyst comprising nickel oxide and molybdenum oxide supported on a suitable carrier can be used. The catalyst carrier can be optionally selected from alumina, silica, silica-alumina and the like. The use of alumina carrier is usually preferred. The preferable amount of catalyst to be supported on a carrier is in the range of 0.5 to 10% by weight as nickel oxide and 3 to 20% by weight as molybdenum oxide. The range of 1 to 5% by weight as nickel oxide and 5 to 16% by weight as molybdenum oxide are more preferable. For example, they can be used by selecting from commercially available alumina supported catalysts of nickel oxide and molybdenum oxide for hydrogenation or desulfurization of hydrocarbons.

The catalysts can be usually used intact without the pre-treatment such as sulfidizing or reducing. However, if necessary, they may be optionally subjected to these pre-treatment.

Dehydrogenation temperature can be suitably selected from the range of 100° C. or higher, preferably 300 to 600° C., more preferably 420 to 530° C., depending on the contact time between catalyst and raw material, and molar ratio of dilution of raw material with diluent. The reaction temperature below 100° C. is economically unfavorable because reaction speed of intended dehydrogenation is too small. On the contrary, excessively high temperature is not suitable for industrial practice because not only dehydrogenation but also decomposition of THI into butadiene or CPD due to reverse Diels-Alder reaction are rapidly accelerated to lower seriously the selectivity and catalytic activity.

In order to promote the reaction by removing hydrogen formed in the reaction system, hydrogen acceptor such as benzene, tetralin, nitrobenzene, cinnamic acid, benzophenone or the like is added to reaction system in a suitable proportion. It is also possible to remove hydrogen formed in dehydrogenation by supplying carbon dioxide or small amount of oxygen into the reaction stream.

Indene formed by the reaction in accordance with the present invention is highly polymerizable, so that a part of indene may be lost due to polymerization or dimerization if a reaction tank is maintained at a high temperature with a high concentration of indene. In order to avoid this defect, it is effective to dilute the concentration of raw materials by entraining an inert gas such as helium, argon or steam into reaction stream. In view of economy and convenience in handling, it is preferable to use steam. Concerning the ratio of dilution with inert gas, there is no particular limitation. It is sufficient if the molar ratio of diluent to raw material THI is more than 1, more preferably more than 20. Although there is no upper limit of the ratio of dilution, excessive dilution is not economical. It is usually below 1,000.

The type of reaction may be any of fix bed, moving bed or fluidized bed. Raw material of THI must be brought into contact with catalyst in vapor phase. In other words, if reaction is carried out in liquid phase, yield is lowered due to the polymerization or dimerization of raw materials or reaction products. In addition, the life of catalyst is seriously shortened due to the deposition of carbon onto the surfaces of catalyst. Therefore, the temperature and pressure of reaction must be selected so as to maintain vapor phase.

Reaction pressure is not particularly limited as long as raw materials and reaction products are vaporized. It is usually in the range of below atmospheric pressure to 10 $kg/cm^2$, preferably below atmospheric pressure to 2 $kg/cm^2$.

The contact time of raw material with catalyst is in the range of 0.005 to 20 seconds, preferably 0.01 to 10 seconds, and more preferably 0.1 to 3 seconds. In the present invention, the average residential time is used as contact time for convenience purpose, with the proviso that catalyst layer is vacant. Contact time of shorter than 0.005 seconds is not preferable because degree of reaction is low. Meanwhile, if contact time is longer than 20 seconds, not only lowering of selectivity due to polymerization of produced indene but also clogging of reactor and heat exchanger in its downstream are caused by polymerized products.

The liquid hourly space velocity (LHSV) of reaction material can be selected from the range of 0.01 to 10 $hr^{-1}$.

In the reaction of the present invention, when catalyst is used for a long period of time, its activity gradually lowers due to coking or else. However, it is possible to recover the original reaction activity by decoking with air at a high temperature of, for example, about 500° C.

In reactor effluent gas containing indene, a large quantity of indane is formed by the removal of one hydrogen molecule from THI as well as small quantities of butadiene, CPD, benzene, toluene, xylene, and DCPD in addition to indene and unreacted THI.

By the way, with regard to indane as a by-product in the above process, it is possible to produce it more effectively by employing relatively mild reaction conditions than those in the foregoing reaction conditions suitable for producing indene. For example, lower dehydrogenation temperature and shorter contact time. Indene can be then produced by dehydrogenating indane.

The gas containing indene that is discharged from reactor is rapidly cooled and liquefied. If necessarily, the gas can be recovered by passing it through an absorbing liquid such as hydrocarbon.

When steam is used as a diluent, it is possible to recover the intended highly pure product by separating water from oil phase and, if necessarily, then subjecting the oil phase to distillation. Because indene is thermally unstable, it must be recovered by a method, in which it does not suffer from high temperature such as distillation under reduced pressure. For example, when distillation is done under reduced pressure for recovering, it is possible to reduce the loss due to thermal polymerization of indene by carrying out the distillation at a reduced pressure with regulating the temperature of distillation still at 140° C. or below. Furthermore, it is also possible to reduce the loss due to unintended polymerization by carrying out distillation with adding a polymerization inhibitor such as BHT or TBC into liquid reaction product.

In the following, the process for producing indene comprising two steps as mentioned in the fifth and subsequent aspects of the present invention will be described in more detail.

As a metallic dehydrogenation catalyst for use in the first step of the present invention, any of known metallic catalysts for dehydrogenation of hydrocarbon can be used. For example, catalyst containing any one of metals selected from nickel, molybdenum, cobalt, chromium, iron, platinum, palladium and ruthenium, their oxides or sulfides, and mixtures of them, can be used. Furthermore, it is preferable that the catalyst does not contain phosphorus. Preferable metallic catalyst is the one containing platinum or palladium, or the one containing any of oxides of metals selected from nickel, molybdenum, cobalt and chromium. More preferable metallic catalysts are those containing oxides of nickel and molybdenum or oxides of cobalt and molybdenum.

The above metallic components can be used by supporting them on a suitable carrier. The catalyst carrier can be selected from alumina, silica, and silica-alumina, wherein alumina is commonly used.

The amount of metal component supported on the carrier is, for example, in the case of metallic catalyst containing oxides of nickel and molybdenum, in the range of 0.5 to 10% by weight as nickel oxide and 3 to 20% by weight as molybdenum oxide, preferably in the range of 1 to 5% by weight as nickel oxide and 5 to 16% by weight as molybdenum oxide.

When the metallic catalyst contains oxides of cobalt and molybdenum, useful catalysts are those containing 1 to 5% by weight cobalt oxide and 3 to 20% by weight as molybdenum oxide, preferably 3 to 5% by weight of nickel oxide and 10 to 14% by weight of molybdenum oxide.

It is possible to use commercially available catalysts, for example, alumina-carrier catalyst containing nickel oxide and molybdenum oxide or alumina-carrier catalyst containing cobalt oxide and molybdenum oxide used for hydrogenation or desulfurization of hydrocarbons.

Further, in order to avoid the coking of catalyst, alkali metal such as potassium can be added to the catalyst for the present invention.

The catalyst can be subjected to pre-treatment such as sulfidization or reduction by a reducing agent such as hydrogen, before using. In the case of catalyst containing platinum or palladium, it is preferable, before using, to pretreat the catalyst with a reducing agent such as hydrogen.

The purpose in the first step of the present invention is mainly to obtain indane through dehydrogenating THI. Indene is also produced as a by-product in the dehydrogenation reaction of THI using metallic catalyst. In this step, however, it is important to raise the yield of indane as an intended product and to lower the yield of indene, although the final purpose is to obtain indene. If the content of indene in the reaction product is high, the catalytic activity is lowered rapidly due to coking and the continuation of long period operation is difficult. Therefore, such operation conditions are employed that the content of indene in reaction product is 10% or less, preferably 5% or less.

Furthermore, in the first step, it is also important to raise conversion efficiency of THI, in which indane is simultaneously produced. If unreacted THI remains in the reaction product, it decomposes into CPD and butadiene due to reverse Diels-Alder reaction in the subsequent second step. As a result, the yield of THI on the basis of concentration of raw material is lowered and as a result, the lowering of catalytic activity is caused. Therefore, it is preferable to attain high conversion efficiency of THI in the first step.

Meanwhile, it is also possible to feed the reaction product of the first step into the second step after reducing the content of THI by distillation. However, it is considerably difficult in industrial practice to reduce selectively the content of THI from the reaction products by distillation because boiling points of THI, indane and indene in reaction products are close to one another; Accordingly, the reaction product of the first step is preferably fed to the second step after subjecting it to only gas separation or the like without any separation or fractionation by distillation. Therefore, it is preferable that the conversion efficiency of THI is made high in the first step to obtain reaction product of low THI content and then it is fed to the second step. In view of these points, the conversion efficiency of THI in the first step is preferably 70% or higher, and more preferably 80% or above.

In order to meet the above-described conditions, the temperature of reaction is suitably selected from the range of 400 to 600° C., preferably 450 to 520° C. depending on the conditions of contact time of raw material with catalyst and molar dilution ratio of diluent to raw material.

The gas discharged from the first step mainly containing indane is immediately liquefied by cooling. If necessarily, the above gas may be recovered by passing it through an absorbing liquid such as hydrocarbon. In some case, the gaseous reaction product can be introduced into a reaction vessel in the second step without cooling.

The gas discharged from the first step containing the main component of indane, contains small quantities of butadiene, CPD, benzene, toluene, xylene and DCPD in addition to indene, unreacted THI and one hydrogen molecule-adduct of THI (the compound having a molecular weight larger than THI by two).

In the second step of the present invention, the reaction product mainly containing indane is used as raw material. Preferable raw materials are those containing main component of indane, preferably 30% by weight or less, more preferably 20% by weight or less of THI and 10% by weight or less of indene, more preferably 5% by weight or less of indene.

It is also possible to obtain highly pure indane from the indane-containing reaction product of the first step through a suitable separation method such as distillation and to use it as the raw material for the second step. It is considered that distillation is suitable as the above-mentioned separation method in industrial practice, however, because the boiling points of THI, indane and indene are close to one another as described above, it is difficult to obtain highly pure indane by distillation. Therefore, it is preferable to use the effluent stream from the first step as the raw material for the second step without applying any treatment. The reaction product resulted from the dehydrogenation reaction that meets the foregoing reaction conditions in the first step, is preferable as the raw material for use in the second step of the present invention.

As metallic catalysts for use in the second step, any catalyst that is known as dehydrogenation catalyst for hydrocarbons, can be employed. Their examples include metallic catalysts containing metals such as nickel, molybdenum, cobalt, chromium, iron, ruthenium, platinum and palladium, oxides or sulfides of these metals, or mixtures of them, which are the same as the catalysts used in the first step. Furthermore, it is preferable that these catalysts are substantially free from phosphorus content.

More specifically, they are exemplified by catalysts containing any one of oxides of metals selected from nickel, molybdenum, cobalt, chromium and iron or metallic catalyst of ruthenium, platinum or palladium. More particularly, they are exemplified by metallic catalyst containing oxides of nickel and molybdenum, metallic catalyst containing oxides of cobalt and molybdenum, metallic catalyst containing chromium oxide or metallic catalyst containing ruthenium oxide.

In the like manner as the foregoing description, metallic components can be used by supporting them on suitable carrier. The catalyst carrier can be optionally selected from the group of alumina, silica and silica-alumina, in which a catalyst carrier of alumina is commonly used.

With regard to the quantity of metallic component supported on a carrier, for example, in the case of metallic catalyst containing oxides of nickel and molybdenum or metallic catalyst containing oxides of cobalt and molybdenum, the same quantity of catalyst as those in the first step can be employed. In other words, in the case of metallic catalyst containing oxides of nickel and molybdenum, catalyst containing 0.5 to 10% by weight as nickel oxide and 3 to 20% by weight as molybdenum oxide can be used. More preferably, catalyst containing 1 to 5% by weight of nickel oxide and 5 to 16% by weight of molybdenum oxide is used.

In this second step, it is possible to use commercially available alumina-supported catalyst containing nickel oxide and molybdenum oxide that is used for hydrogenation or desulfurization of hydrocarbons. By the way, it is also possible to use the same catalyst as that used in the first step.

The reaction temperature in the second step can be selected from the range of 500 to 650° C., preferably 550 to 600° C. depending on the contact time of raw material with catalyst or molar dilution ratio of diluent to raw material. In the case that the catalytic activity is lowered with the passage of reaction time, it is preferable to raise reaction temperature gradually.

The gas discharged from the second step containing the main component of indene is liquefied by rapid cooling. If necessarily, the above gas may be recovered by passing it through an absorbing liquid such as hydrocarbon. Meanwhile, the gas discharged from the second step containing the main component of indene, also contains small quantities of unreacted THI, butadiene, CPD, benzene, toluene, xylene and DCPD as well as indane.

In the foregoing first step and second step, it is possible to employ the same conditions to each other concerning removal of hydrogen from reaction system, diluent for reaction, type of reaction, reaction pressure, contact time of raw material with catalyst, liquid hourly space velocity (LHSV) of raw material, method of activation of catalyst, recovery method by distillation and so forth. Although these conditions overlap with the conditions as described concerning the methods of second aspect to fourth aspect of the present invention, they will be repeatedly described as follows.

In the first place, in order to promote the reaction by removing hydrogen formed in the reaction system, hydrogen acceptor such as benzene, tetralin, nitrobenzene, cinnamic acid or benzophenone is added. It is also possible to remove the formed hydrogen by feeding carbon dioxide or small quantity of oxygen into reaction stream.

Not only in the second step but also in the first step as described in the foregoing paragraph, in addition to indane, indene is partially produced as a by-product by the dehydrogenation of THI. The formed indene is highly polymerizable, so that it is lost due to its partial polymerization or dimerization when reaction vessel is maintained at high temperature with high indene content. Therefore, it is preferable to dilute the concentration of raw material by using inert gas, particularly steam. As previously described, the molar ratio of diluent to raw material of 1 or more is sufficient, and more preferably more than 20.

The type of reaction may be any of fix bed, moving bed and fluid bed. The raw material of THI is brought into contact with catalyst in vapor phase. It is not preferable to carry out the reaction in liquid phase, because yield becomes low due to polymerization or dimerization of raw material or reaction product and, in addition, catalytic life is seriously shortened due to the deposition of carbon on the surfaces of catalyst.

Reaction pressure is not particularly limited as long as raw material and reaction product are vaporized. It is usually in the range of below atmospheric pressure to 10 $kg/cm^2$, preferably below atmospheric pressure to 2 $kg/cm^2$.

The contact time of raw material with catalyst is in the range of 0.005 to 20 seconds, preferably 0.01 to 10 seconds, and more preferably 0.1 to 3 seconds. If the contact time is shorter than 0.005 second, it is not preferable because reaction efficiency is low. While, if the contact time is longer than 20 seconds, it occurs not only that selectivity is low due to polymerization of formed indene but also that reactor and heat exchanger on its downstream side are sometimes blocked with polymerization product.

The liquid hourly space velocity (LHSV) of reaction material can be selected from the range of 0.01 to 10 $hr^{-1}$.

In the reaction according to the present invention, when catalyst is used for long period of time, its activity may be gradually lowered due to coking or else. In such a case, it is possible to recover the initial reaction activity by conducting decoking using air or the like at high temperature, for example, at about 500° C.

When steam is used as diluent, a mixture of water and oily components is obtained. The oily components are recovered by separating water from oily components by a suitable separation method such as the separation using a settling tank. In the first step, the recovered oily components can be used intact as raw material for the second step. It is also possible, if necessarily, to recover the intended product of highly pure indane from the oily components by distillation. In case of the second step, if necessarily, the aimed product can be recovered in high purity by distillation.

In distillation, indene contained in reaction product is subject to thermal polymerization, so that it is liable to cause the clogging of distillation apparatus with polymerized product. Therefore, it is necessarily to employ a recovering method that can be carried out at low temperature such as reduced pressure distillation. For example, when recovering is done by reduced pressure distillation, it is possible to reduce the loss due to thermal polymerization of indene by carrying out distillation under a reduced pressure with regulating the temperature of distillation still at temperature not higher than 140° C. Furthermore, the loss due to polymerization can also be reduced by carrying out distillation with adding polymerization inhibitor such as BHT or TBC into liquid reaction product.

BEST METHOD OF CARRYING OUT THE EMBODIMENT OF THE INVENTION

The present invention will be described in more detail with reference to the following examples. In the following description, "%" means "% by weight".

EXAMPLE 1

The particle size of nickel oxide/molybdenum oxide catalyst (composed of 1.5% of nickel oxide, 7.4% of molybdenum trioxide and alumina carrier; made by Catalysts & Chemicals Industries Co., Ltd.; trade name: CDS-DM5CT) was adjusted to 16 to 20 mesh. 25 ml of the catalyst was filled into a stainless steel tube of 12 mm in inside diameter and 1 m in length. THI with a flow rate of 22.3 g/hr and water with a flow rate of 72 ml/hr were passed through the catalyst bed at atmospheric pressure by way of a preheating tube at 500° C. The contact time with the catalyst was 0.34 second.

The reaction gas was then cooled to room temperature and gas and water were separated from organic layer. The weight of organic phase was measured and the concentrations of indene, THI, butadiene and CPD were analyzed by Gas chromatography (GC). The results of analysis of effluent oil samples at 1, 2, 3, 4, 5, 6 and 24 hours after start of charging are shown in the following Table 1.

The recovery rate in Table 1 indicates that of oily components that was obtained by cooling the produced gas. The nonrecoverable components are mainly gaseous.

Obtained organic phase was subjected to reduced pressure distillation with a distillation tower filled with Helipack to recover a fraction having boiling points of 60.4 to 62.5° C. at a reduced pressure of 10 torr. According to the result of GC analysis, this fraction contained 99.1% of indene and in addition, 0.9% of indane.

EXAMPLE 2

Reaction was carried out in the like manner as in Example 1 except that reaction temperature was 480° C. and flow rate of water was 36 ml/hr. The sample taken at 2 hours after the start of operation was analyzed. The results of analysis are shown in Table 1.

Comparative Example 1

Reaction was carried out in the like manner as in Example 1 except that cobalt oxide/molybdenum oxide catalyst (composed of 3.5% of cobalt oxide, 10% of molybdenum trioxide and alumina carrier; made by Nissan Girdler Catalyst Co., Ltd.; trade name: G-51B) was. used as catalyst. The results of analysis of effluent oil samples taken at 1, 2, 3, 4, 5 and 6 hours after start of charging are shown in Table 1.

Comparative Examples 2 and 3

Reaction was carried out the like manner as in Example 1 except that reaction temperatures were set at 550° C. and 400° C., respectively. The results of analysis of effluent oil samples taken at 2 hours after start of charging are shown in Table 1.

Comparative Example 4

Reaction was carried out in the like manner as in Example 1 except that cobalt oxide/molybdenum oxide catalyst (made by Nissan Girdler Catalyst Co., Ltd.; trade name: G-51B) was used and reaction temperature was kept at 550° C. The sample taken at 2 hours after the start of operation was analyzed. The results of analysis are shown in Table 1.

TABLE 1

| | Sampling Time (hr) | Recovery Rate (%) | Composition of Recovered Oil (%) | | |
|---|---|---|---|---|---|
| | | | THI | Indene | Butadiene + CPD |
| Example 1 | 1 | 86 | 0.8 | 23.9 | 2.2 |
| | 2 | 87 | 0.9 | 21.1 | 2.3 |
| | 3 | 90 | 0.9 | 19.9 | 2.5 |
| | 4 | 95 | 1.0 | 18.6 | 2.5 |
| | 5 | 91 | 1.1 | 18.2 | 2.6 |
| | 6 | 90 | 1.3 | 16.8 | 2.4 |
| | 24 | 96 | 1.4 | 13.7 | 1.8 |
| Example 2 | 2 | 98 | 0.8 | 20.9 | 3.0 |
| Comparative Example 1 | 1 | 90 | 0 | 15.2 | 2.8 |
| | 2 | 92 | 0 | 14.1 | 3.4 |
| | 3 | 89 | 0 | 11.6 | 3.3 |
| | 4 | 92 | 0 | 10.2 | 3.9 |
| | 5 | 90 | 0 | 9.5 | 4.2 |
| | 6 | 92 | 0 | 7.1 | 3.3 |
| Comparative Example 2 | 2 | 53 | 5.7 | 40.3 | 35.3 |
| Comparative Example 3 | 2 | 92 | 3.4 | 0.5 | 0.2 |
| Comparative Example 4 | 2 | 51 | 3.3 | 20.0 | 67.1 |

EXAMPLE 3

Reaction comprising two steps was carried as follows.
(First Step)

The particle size of nickel oxide/molybdenum oxide catalyst (trade name: CDS-D5CT; made by Catalysts & Chemicals Industry Co., Ltd.) was adjusted to 16 to 20 mesh. 25 ml of the catalyst was filled into a stainless steel tube of 12 mm in inside diameter and 1 m in length. THI with a flow rate of 22.3 g/hr and water with a flow rate of 72 ml/hr were passed through the catalyst bed at atmospheric pressure by way of a preheating tube at 450° C. The contact time with the catalyst was 0.39 second.

The reaction gas was then cooled to room temperature and gas and water were separated from organic layer. The weight of organic phase was measured and the concentrations of indane, indene, THI, butadiene and CPD were analyzed by GC. The results of analysis of effluent oil samples at 2, 4, 6 and 24 hours after start of charging are shown in the following Table 2.

(Second Step)

The particle size of nickel oxide/molybdenum oxide catalyst (trade name: CDS-DM5CT; made by Catalysts & Chemicals Industry Co., Ltd.) was adjusted to 16 to 20 mesh. 25 ml of the catalyst was filled into a stainless steel tube of 12 mm in inside diameter and 1 m in length. The organic phase obtained in First Step with a flow rate of 23 g/hr and water with a flow rate of 72 ml/hr were passed through the catalyst bed at atmospheric pressure by way of a preheating tube at 550° C. The contact time with the catalyst was 0.32 second.

The reaction gas was then cooled to room temperature and gas and water were separated from organic layer. The weight of organic phase was measured and the concentrations of indane, indene, THI, butadiene and CPD were analyzed by GC. The results of analysis of effluent oil samples taken at 2, 4, 6 and 24 hours after start of charging are shown in the following Table 2.

Obtained organic phase was subjected to reduced pressure distillation with a distillation tower filled with Helipack to recover a fraction having boiling points of 60.4 to 62.5° C. at a reduced pressure of 10 torr. According to the result of GC analysis, this fraction contained 99.1% of indene and in addition, 0.9% of indane.

EXAMPLES 4-1, 4-2, AND 4-3

(First Step)

Reaction was carried out in the like manner as in First Step of Example 3 except that cobalt oxide/molybdenum oxide catalyst (made by Nissan Girdler Catalyst Co., Ltd.; trade name: G-51B) was used as catalyst. The samples taken at 2 hours after the start of operation were analyzed. The results of analysis are shown in Table 2.

(Second Step)

Reaction was carried out in the like manner as in Second Step of Example 3 except that combinations of catalysts and reaction temperatures were changed as follows. In Example 4-1, cobalt oxide/molybdenum oxide catalyst (made by Nissan Girdler Catalyst Co., Ltd.; trade name: G-51B) was used at reaction temperature of 500° C. In Example 4-2, chromium oxide/alumina catalyst (containing 10% of chromium oxide; made by Nissan Girdler Catalyst Co., Ltd.; trade name: G-41P) was used at reaction temperature of 550° C. In Example 4-3, ruthenium/alumina catalyst (containing 0.5% of ruthenium; made by N. E. Chemcat Co., Ltd.) was used at reaction temperature of 570° C. The samples taken at 2 hours after the start of operation were analyzed. The results of analysis are shown in Table 2.

EXAMPLE 5

(Continuous Reaction of First Step and Second Step Using Crude THI as Raw Material)

Reaction was carried out in the like manner as in First Step of Example 3 using by-product (THI content: 66.9%) of producing vinyl norbornene with the reaction of butadiene and CPD. Liquid reaction product containing 43.7% of indane was obtained. Using this as raw material, reaction was carried out again in the like manner as in Second Step of Example 3. As a result, liquid reaction product containing 39.4% of indene and 35.7% of indane was obtained.

TABLE 2

|  | Example 3 | | | | Example 4 | | |
|---|---|---|---|---|---|---|---|
|  |  |  |  |  | 4-1 | 4-2 | 4-3 |
| First Step |  |  |  |  |  |  |  |
| Catalyst[1] | A | | | | B | B | B |
| Sampling Time (hr) | 2 | 4 | 6 | 24 | 2 | 2 | 2 |
| Temperature (° C.) | 450 | 450 | 450 | 450 | 450 | 450 | 450 |
| Recovery Rate (%) | 97.0 | 96.1 | 94.3 | 95.0 | 98.0 | 98.0 | 98.0 |
| Recovered Composition |  |  |  |  |  |  |  |
| Indane (%) | 82.5 | 81.5 | 80.6 | 77.9 | 84.0 | 84.0 | 84.0 |
| THI (%) | 1.4 | 1.5 | 1.8 | 2.0 | 0.1 | 0.1 | 0.1 |
| Indene (%) | 4.7 | 4.2 | 3.4 | 4.2 | 3.2 | 3.2 | 3.2 |
| Butadiene + CPD (%) | 0.6 | 0.7 | 0.7 | 0.8 | 1.3 | 1.3 | 1.3 |
| Second Step |  |  |  |  |  |  |  |
| Catalyst[1] | A | | | | B | C | D |
| Sampling Time (hr) | 2 | 4 | 6 | 24 | 2 | 2 | 2 |
| Temperature (° C.) | 550 | 550 | 550 | 570 | 500 | 550 | 570 |
| Recovery Rate (%) | 85.0 | 91.5 | 92.7 | 89.9 | 97.0 | 79.3 | 95.0 |
| Recovered Composition |  |  |  |  |  |  |  |
| Indane (%) | 42.7 | 43.6 | 46.5 | 53.5 | 65.7 | 35.9 | 42.8 |
| THI (%) | 0.7 | 0.8 | 0.9 | 1.2 | 0.8 | 1.2 | 1.3 |
| Indene (%) | 48.9 | 49.5 | 45.1 | 35.7 | 31.9 | 55.7 | 53.7 |
| Butadiene + CPD (%) | 0.5 | 0.3 | 0.3 | 0.4 | 0.5 | 2.3 | 0.6 |

Remarks:
(1) Catalyst:
A: nickel oxide/molybdenum oxide (CDS-DM5CT)
B: Cobalt oxide/molybdenum oxide (G-51B)
C: Chromium oxide (G-41P)
D: Ruthenium

Industrial Applicability

With the method of the present invention, it is possible to produce indene, which is useful as a raw material for producing transparent and highly heat resistant resin or as raw material for ligands of single site catalyst used in the polymerization for producing polyolefins. It is advantageous in that highly pure indene can be prepared by a simple reaction process from inexpensive raw material.

What is claimed is:

1. A process for producing indene in high yields with less deterioration of catalyst, which process comprises dehydrogenating tetrahydroindene in a vapor phase and in the presence of a metallic dehydrogenation catalyst comprising nickel oxide and molybdenum oxide.

2. A process for producing indene in claim 1, wherein said dehydrogenation is carried out at a temperature of 100°C or above using a catalyst consisting of nickel oxide and molybdenum oxide.

3. A process for producing indene in claim 2, wherein said dehydrogenation is carried out at a temperature in the range of 420 to 530° C.

4. A process for producing indene in claim 2, wherein said dehydrogenation is carried out at a pressure in the range of below atmospheric to 10 kg/cm$^2$.

5. A process for producing indene according to claim 2, wherein said catalyst comprises from 0.5–10%, by weight, of an oxide of nickel and from 3–20%, by weight, of an oxide of molybdenum.

6. A process for producing indene according to claim 5, wherein said catalyst comprises from 1–5%, by weight, of an oxide of nickel and from 5–16%, by weight, of an oxide of molybdenum.

7. A process for producing indene which comprises the following First Step and Second Step:

(First Step) a process for producing a reaction product containing a main component of indane while suppressing the formation of indene by dehydrogenating tetrahydroindene in a vapor phase in the presence of a metallic dehydrogenation catalyst comprising nickel oxide and molybdenum oxide, and (Second Step) a process for producing indene by dehydrogenating the reaction product obtained in said First Step in a vapor phase and in the presence of a metallic dehydrogenation catalyst.

8. A process for producing indene in claim 7, wherein the content of indane in the reaction product obtained in said First Step is 70% by weight or more.

9. A process for producing indene in claim 7, wherein the content of indene in the reaction product obtained in said First Step is 10% by weight or less.

10. A process for producing indene according to claim 9, wherein the content of indene in the reaction product obtained in said First Step is 5% by weight or less.

11. A process for producing indene in claim 7, wherein the metallic dehydrogenation catalyst used in said Second Step is a metallic oxide catalyst containing oxide of any one of metal selected from the group consisting of nickel, molybdenum, cobalt and chromium.

12. A process for producing indene in claim 11, wherein the metallic dehydrogenation catalyst used in said Second Step is a catalyst containing oxides of nickel and molybdenum or oxides of cobalt and molybdenum.

13. A process for producing indene in claim 7, wherein the metallic dehydrogenation catalyst used in said Second Step is a catalyst containing ruthenium.

14. A process for producing indene according to claim 7, wherein the said catalyst in said First Step does not contain phosphorus.

15. A process for producing indene according to claim 7, wherein an alkali metal is added to the said catalyst used in said First Step.

16. A process for producing indene according to claim 7, wherein said dehydrogenation catalyst of the first step is a metallic oxide containing an oxide of nickel and an oxide of molybdenum, which catalyst comprises from 0.5–10%, by weight, of an oxide of nickel and from 3–20%, by weight, of an oxide of molybdenum.

17. A process for producing indene according to claim 7, wherein in said First Step dehydrogenation is carried out at a temperature in the range of 400–600° C. and wherein the contact time of raw material with catalysts ranges from 0.005 to 20 seconds.

18. A process for producing indene according to claim 7 wherein the reaction product obtained in said First Step is subjected to gas separation without any separation or fractionation by distillation and fed to said Second Step, said Second Step is carried out at a temperature of 550° C. to 600° C., and said First and Second Steps are conducted at a pressure of below atmospheric pressure to 10 kg/cm$^2$.

* * * * *